United States Patent
Yang

(10) Patent No.: US 8,502,683 B2
(45) Date of Patent: Aug. 6, 2013

(54) DEVICE AND METHOD FOR REMOTE MONITORING

(75) Inventor: Jiang-Chao Yang, Shenzhen (CN)

(73) Assignees: Shenzhen Futaihong Precision Industry Co., Ltd., Shenzhen (CN); Chi Mei Communication Systems, Inc., New Taipei (TW)

( * ) Notice: Subject to any disclaimer, the term of this patent is extended or adjusted under 35 U.S.C. 154(b) by 618 days.

(21) Appl. No.: 12/772,996

(22) Filed: May 3, 2010

(65) Prior Publication Data

US 2010/0280391 A1  Nov. 4, 2010

(30) Foreign Application Priority Data

May 4, 2009 (CN) .......................... 2009 1 0302092

(51) Int. Cl.
G08B 23/00 (2006.01)
(52) U.S. Cl.
USPC ...................... 340/573.4; 340/573.1; 600/473

(58) Field of Classification Search
None
See application file for complete search history.

(56) References Cited

U.S. PATENT DOCUMENTS

| 6,049,281 A * | 4/2000 | Osterweil | 340/573.4 |
| 2009/0189771 A1 * | 7/2009 | Liu | 340/573.1 |

FOREIGN PATENT DOCUMENTS

| JP | 10259942 A | * | 9/1998 |
| JP | 2003299636 A | * | 10/2003 |

* cited by examiner

*Primary Examiner* — Brian Zimmerman
*Assistant Examiner* — Kevin Lau
(74) *Attorney, Agent, or Firm* — Altis Law Group, Inc.

(57) ABSTRACT

An electronic device and a method for remote monitoring a subject calibrates a permitted activity range of the electronic device and establishes an activity range of the subject. The electronic device captures a thermal image to calculate a current location of the subject, and determines whether the current location of the subject is within the activity range of the subject. The electronic device issues an alarm message if the current location of the subject is not within the activity range of the subject.

15 Claims, 4 Drawing Sheets

DEVICE AND METHOD FOR REMOTE MONITORING

BACKGROUND

1. Technical Field

Embodiments of the present disclosure relate to monitoring, and more particularly to a device and method for remote monitoring.

2. Description of Related Art

Systems for remote monitoring have been developed to monitor the condition of sleeping infants and other situations such that the situations can be supervised without actual presence in the location. However, continuous monitoring can be inconvenient.

DETAILED DESCRIPTION

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

In general, the word "module" as used herein, refers to logic embodied in hardware or firmware, or to a collection of software instructions, written in a programming language, such as, for example, Java, C, or assembly. One or more software instructions in the module may be embedded in firmware, such as an EPROM. It will be appreciated that module may comprise connected logic units, such as gates and flip-flops, and may comprise programmable units, such as programmable gate arrays or processors. The module described herein may be implemented as either software and/or hardware module and may be stored in any type of computer-readable medium or other computer storage device.

Figure 1:
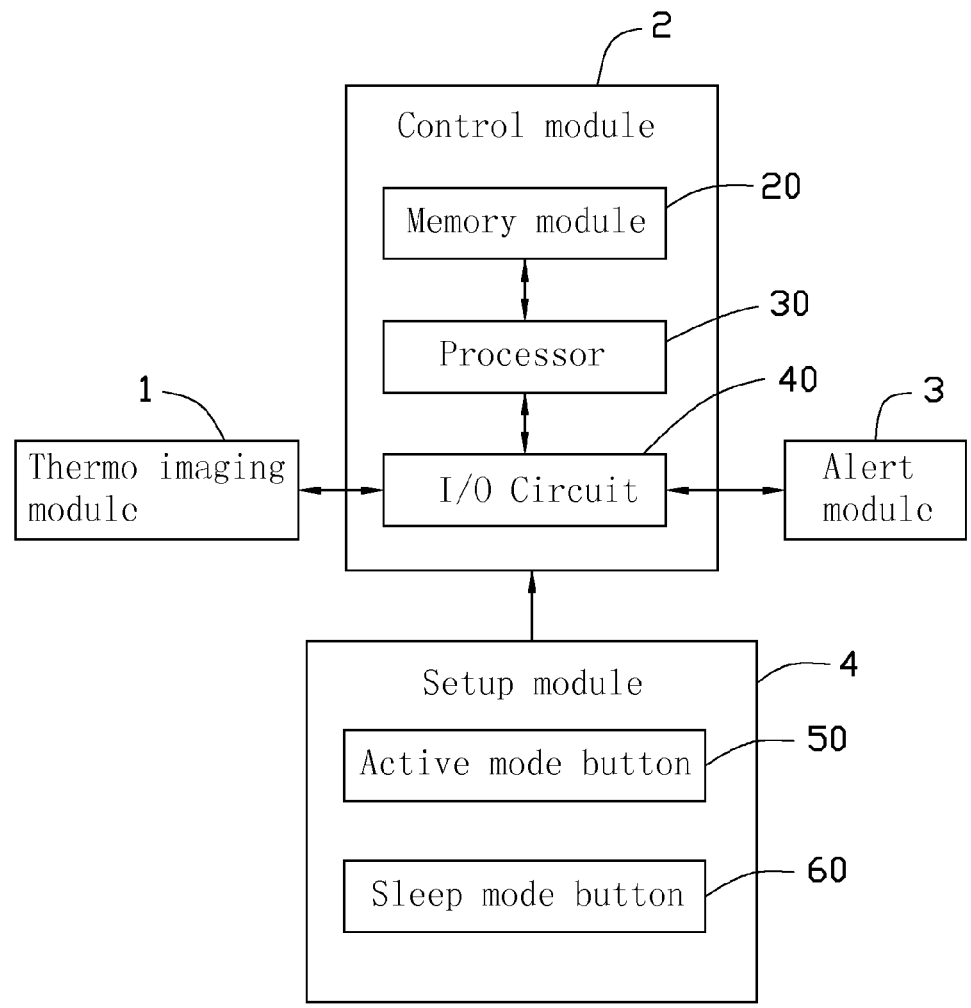
FIG. 1 is a block diagram of one embodiment of a remote monitoring device.

FIG. 1 is a block diagram of one embodiment of a remote monitoring device 100. The remote monitoring device 100 is developed to monitor the condition of sleeping infants and other situations such that the situations can be supervised without actual presence in the location. The remote monitoring device 100 includes a thermal imaging module 1, a control module 2, an alert module 3 and a setup module 4.

The remote monitoring device 100 is generally controlled and coordinated by operating system software, such as the UNIX, Linux, Windows 95, 98, NT, 2000, XP, Vista, Mac OS X, an embedded operating system, or any other compatible operating systems. In other embodiments, the electronic device 1 may be controlled by a proprietary operating system. Conventional operating systems control and schedule computer processes for execution, perform memory management, provide file system, networking, and I/O services, and provide a user interface, such as a graphical user interface (GUI), among other things.

The thermal imaging module 1 is operable to capture a thermal image of the subject and measure a corresponding temperature and coordinate values of each pixel in the thermal image. The control module 2 is operable to determine whether activity of the subject is within a permitted range. In addition, the control module 2 is operable to determine if an exposed area of the subject (e.g., an area of the subject not under a blanket) exceeds a predefined exposed area, potentially providing alarm message that a sleeping subject may be uncovered. The alert module 3 is operable to send an alert message to a user when detecting an abnormal situation. The setup module 4 is operable to set modes of the remote monitoring device 100. In one embodiment, the modes include an active mode and a sleep mode. The active mode is to monitor an activity range of a subject while the subject is in an active mode. The sleep mode is to monitor a subject while in sleep mode.

The control module 2 includes a memory module 20, a processor 30 and an input/output (I/O) circuit 40. The control module 2 is configured to connect to the thermal imaging module 1, the alert module 3 and the setup module 4 by the I/O circuit 40. The control module 2 is configured to set a predetermined temperature and to detect points of the thermal image exceeding that temperature. For example, the predetermined temperature may be set to be 36° C., being a normal body temperature for a child at rest.

The setup module 4 includes an active mode button 50 and a sleep mode button 60. The remote monitoring device 100 operates in the active mode when the active mode button 50 is pressed. The remote monitoring device 100 operates in the sleep mode when the sleep mode button 60 is pressed.

Figure 2:
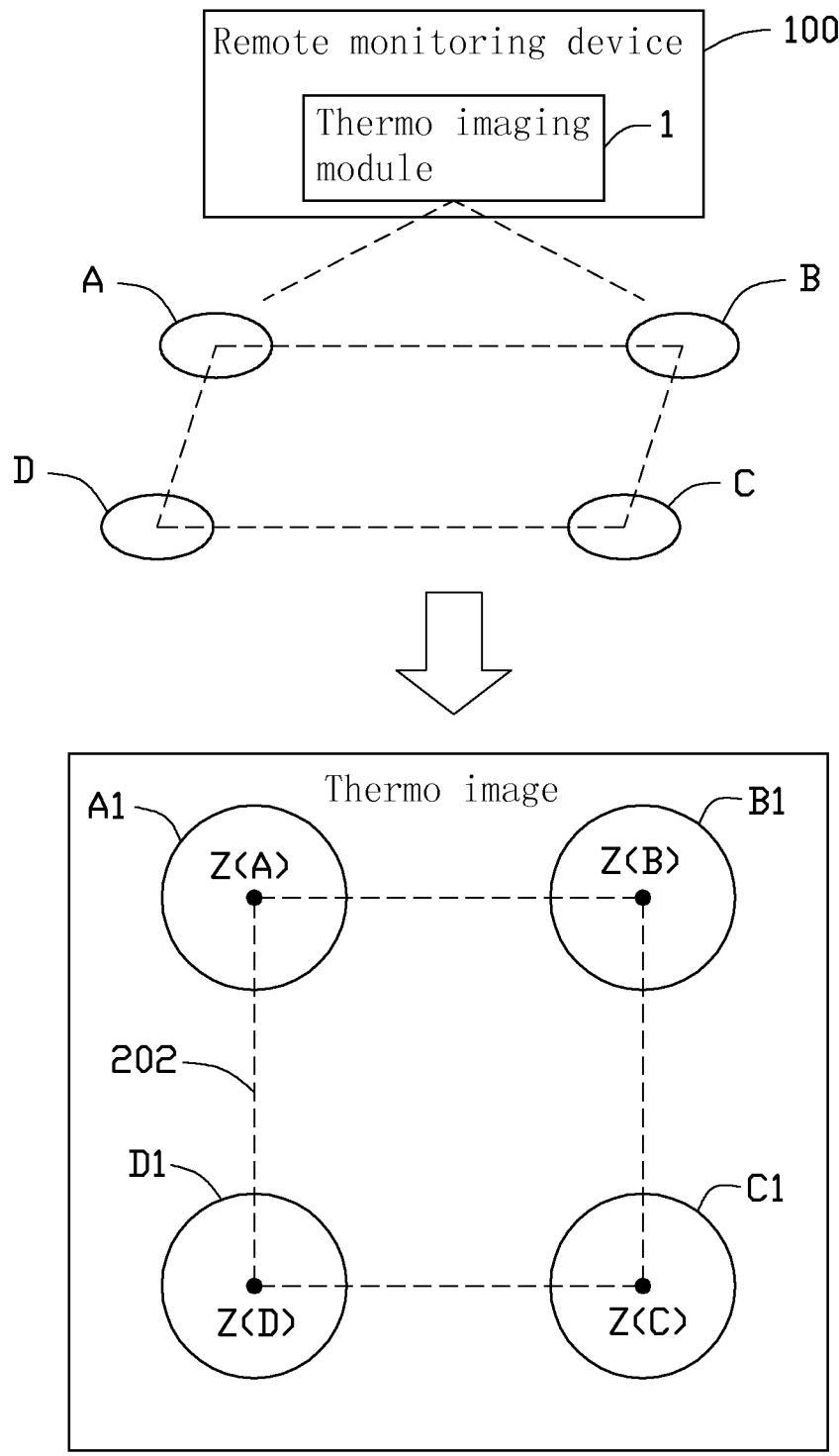
FIG. 2 is a schematic diagram of the remote monitoring device of FIG. 1 monitoring a subject while in active mode.

FIG. 2 is a schematic diagram of the remote monitoring device 100 of FIG. 1 monitoring a subject while in active mode. As shown, the thermal imaging module 1 is positioned above the activity range, as indicated by A, B, C and D, of the subject. It is to be noted that the permitted activity range of the subject may be calibrated by the control module 2. In one embodiment, the thermal imaging module 1 captures the thermal image of the subject in position A. The control module 2 then detects points with temperature exceeding 36° C. to form a figure A1. After obtaining figure A1, the control module 2 executes a calibration function to calculate the average value of the position coordinates Z(A) of figure A1.

Accordingly, the thermal imaging module 1 captures respective thermal images at points B, C, and D. Repeating the described process for generating Z(A), the control module 2 forms figures B1, C1, and D1 respectively and calculates the average value of the position coordinates Z(B), Z(C) and Z(D). As shown in FIG. 2, the square 202 Z(A), Z(B), Z(C) and Z(D) defines a permitted activity range of the subject. In other embodiments, the thermal imaging module 1 captures a thermal image from the subject. Repeating the process described, the control module 2 continuously calculates locations of the subject from the captured images.

The control module 2 compares the calculated location of the subject with the permitted activity range of the subject. If the calculated location of the subject is not within the permitted activity range of the subject, the control module 2 directs alert module 3 to issue an alarm message. If the calculated location of the subject is within the permitted activity range, the thermal imaging module 1 captures an image of the moving subject and the control module 2 continually reads subsequent captured images to determine if the calculated location of the subject is within the permitted activity range.

Figure 3:
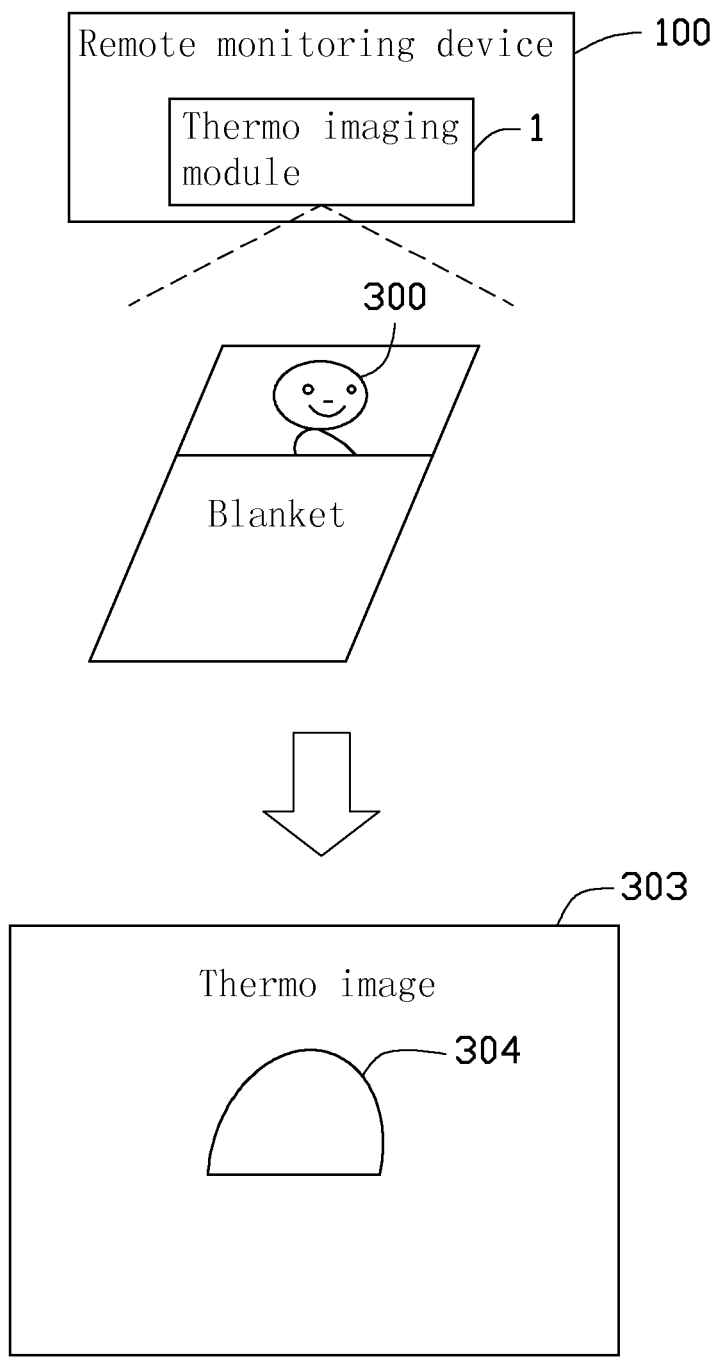
FIG. 3 is a schematic diagram of the remote monitoring device of FIG. 1 monitoring a subject while in sleep mode.

FIG. 3 is a schematic diagram of the remote monitoring device 100 of FIG. 1 monitoring a subject while in sleep mode. As shown in FIG. 3, the subject is positioned on a bed and partially covered by a blanket. The processor 30 sets a predetermined temperature below the normal body temperature of a subject at rest. The thermal imaging module 1 captures a thermal image 303 of the covered sleeping subject after the sleep mode button 60 is pressed. The control module 2 then reads the thermal image 303 and detects the points with temperature exceeding the predetermined temperature.

The processor 30 calculates the exposed area outside the blanket of the subject based on the detected points and to form the exposed area 304. The memory module 20 saves the information of the exposed area 304. After obtaining the thermal image, the processor 30 determines if the exposed area 304 is less than the predefined exposed area, and, if so, the control module 2 continually reads subsequent captured images. If the exposed area 304 exceeds the predefined exposed area, the control module 2 activates alert module 3 and alarm message is issued.

Figure 4:
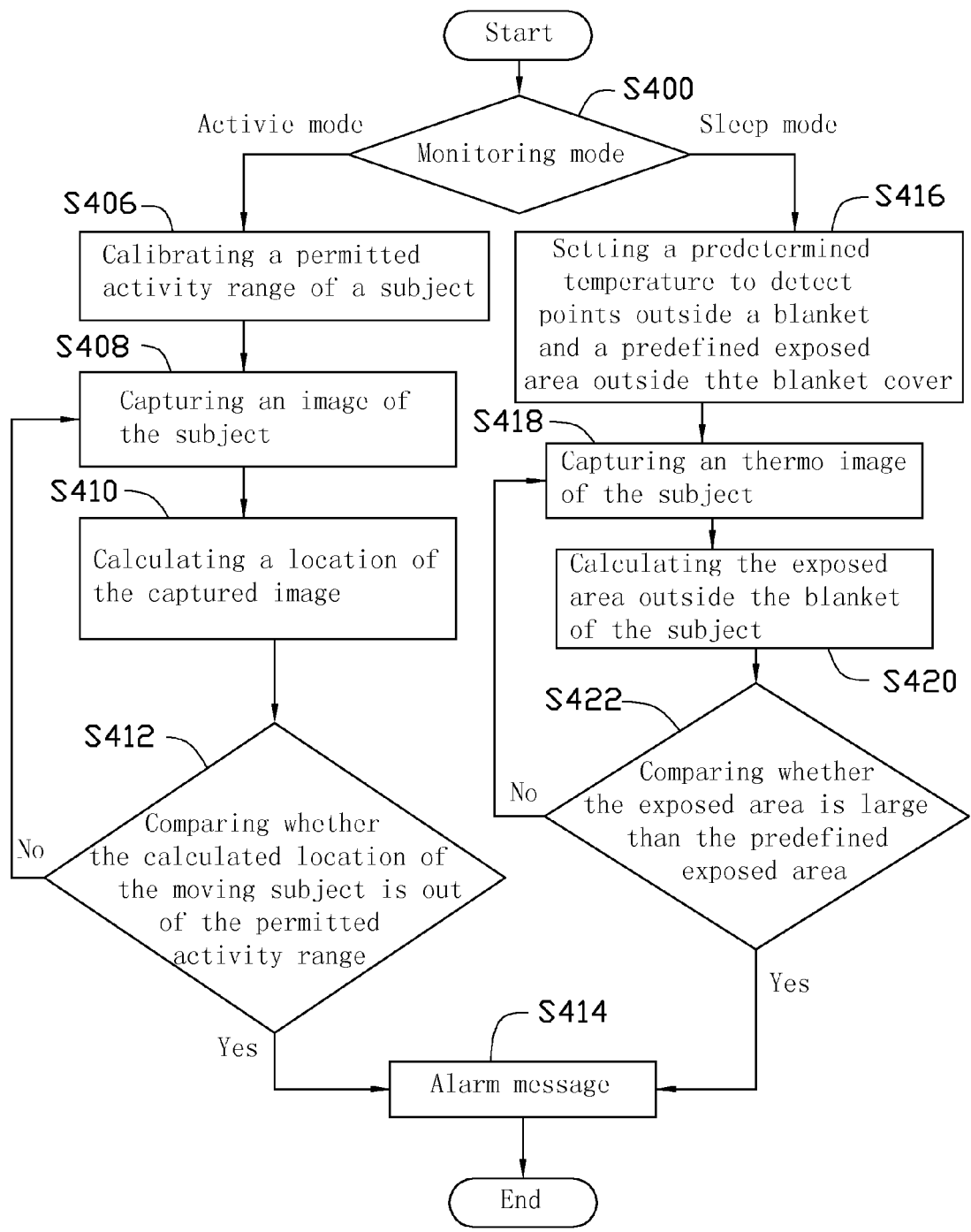
FIG. 4 is a flowchart illustrating one embodiment of a method of remote monitoring using an electronic device.

FIG. 4 is a flowchart illustrating an embodiment of a method of monitoring a subject by an electronic device. Depending on the embodiment, additional blocks may be added, others deleted, and the ordering of the blocks may be changed.

In block S400, the setup module 4 sets modes of the remote monitoring device 100. If the remote monitoring device 100 is set to active mode, block S406 is implemented. If the remote monitoring device 100 is set to sleep mode, block S416 is implemented.

In block S406, the control module 2 calibrates a permitted activity range of the subject.

In block S408, the thermal imaging module 1 captures an image of the subject and reads corresponding temperature and coordinate values of each pixel from the thermal image.

In block S410, the control module 2 calculates a location of the captured image.

In block S412, the control module 2 determines whether the calculated location of the subject is within of the permitted activity range of the subject. If not, in block S414, the control module 2 activates alert module 3 to issue an alarm message. If so, block S408 is implemented and subsequent images of the subject are captured.

If the remote monitoring device 100 is set to sleep mode, block S416 is implemented, in which control module 2 sets a predetermined temperature to which temperatures of points outside the blanket and a predefined exposed area outside a blanket can be compared.

In block S418, the thermal imaging module 1 captures a thermal image 303 of the subject.

In block S420, the control module 2 reads the thermal image 303 and detects points with temperature exceeding the predetermined temperature. The control module 2 then calculates the exposed area outside the blanket of the subject to form the exposed area 304.

In block S422, the control module 2 determines whether the exposed area 304 exceeds the predefined exposed area. If so, in block S414, the control module 2 activates alert module 3. If not, block S418 is implemented.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. A method for remote monitoring of a subject by an electronic device, the method comprising:
   calibrating a permitted activity range of the subject by capturing four thermal images of the subject in four predetermined positions, detecting points with temperature exceeding a predetermined temperature in each of the four thermal images to form four figures, determining four central positions of the four figures, and determining a square based on the four central positions of the four figures so that define the permitted activity range of the subject;
   capturing a thermal image using a thermal imaging module, to calculate a current location of the subject;
   determining whether the current location of the subject is within the permitted activity range; and
   issuing an alarm message if the current location of the subject is not within the permitted activity range of the subject.

2. The method of claim 1, wherein the location of the subject is determined by detecting an exposed area of the subject having a temperature exceeding the predetermined temperature.

3. The method of claim 2, wherein the location of the subject is determined by calculating an average value of points within the exposed area.

4. The method of claim 1, further comprising:
   setting the predetermined temperature to detect points outside a predetermined area;
   setting a predefined exposed area outside the predetermined area after monitoring the subject in a sleeping status;
   capturing a thermal image and calculating the exposed area outside the predetermined area of the subject;
   determining whether the exposed area exceeds the predefined exposed area; and
   issuing an alarm message if the exposed area exceeds the predefined exposed area.

5. The method of claim 4, further comprising reading the thermal image and detecting points having a temperature exceeding a predetermined temperature.

6. The method of claim 4, wherein the step of calculating the exposed area is a sum calculation of the exposed area.

7. An electronic device providing remote monitoring of a subject, the electronic device comprising:
   a setup module to set modes of the electronic device;
   a thermal imaging module to capture at least one thermal image from the subject and to acquire temperature and coordinates from the thermal images;
   a control module to calibrate a permitted activity range of the subject by capturing four thermal images of the subject in four predetermined positions, detecting points with temperature exceeding a predetermined temperature in each of the four thermal images to form four figures, determining four central positions of the four figures, and determining a square based on the four central positions of the four figures so that define the permitted activity range of the subject, to calculate an activity range of the subject and to calculate a current location of the subject from the captured thermal image; and
   an alert module to issue an alarm message if the control module detects the location of the subject is outside the activity range of the subject.

8. The electronic device of claim 7, wherein the control module reads the thermal image and acquires positions in which current temperature exceeds the predetermined temperature as within the activity range of the subject.

9. The electronic device of claim 7, wherein the control module calculates the current location of the subject by an average value of the position coordinates.

10. The electronic device of claim 7, wherein the setup module further establishes a predefined exposed area upon monitoring the subject sleeping.

11. The electronic device of claim 7, wherein the control module further reads a thermal image, calculates an exposed area of the subject and determines whether the exposed area exceeds the predefined exposed area.

12. The electronic device of claim 7, wherein the alarm module further issues an alarm message upon detecting that an exposed area exceeds the predefined exposed area.

13. A non-transitory computer-readable storage medium having stored thereon instructions that, when executed by a processor, causes the processor to perform a method for remote monitoring of a subject by an electronic device, the method comprising:

calibrate a permitted activity range of the subject by capturing four thermal images of the subject in four predetermined positions, detecting points with temperature exceeding a predetermined temperature in each of the four thermal images to form four figures, determining four central positions of the four figures, and determining a square based on the four central positions of the four figures so that define the permitted activity range of the subject;

establish a predefined exposed area after monitoring the subject in a sleeping status;

capture a thermal image and calculating the exposed area of the subject;

determine whether the exposed area exceeds the predefined exposed area; and issue an alarm message if the exposed area exceeds the predefined exposed area.

14. The non-transitory computer-readable storage medium of claim 13, wherein the method further comprising:

read the thermal image and detecting points with temperature exceeding the predetermined temperature.

15. The non-transitory computer-readable storage medium of claim 13, wherein the step of calculate the exposed area is a sum calculation of the exposed area.

\* \* \* \* \*